United States Patent
West et al.

(10) Patent No.: US 8,027,148 B2
(45) Date of Patent: Sep. 27, 2011

(54) ORGANOSILICON AMINE-BASED ELECTROLYTES

(75) Inventors: Robert C. West, Madison, WI (US); Lingzhi Zhang, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 9 days.

(21) Appl. No.: 12/710,381

(22) Filed: Feb. 23, 2010

(65) Prior Publication Data
US 2010/0149726 A1 Jun. 17, 2010

Related U.S. Application Data

(62) Division of application No. 11/865,089, filed on Oct. 1, 2007, now abandoned.

(51) Int. Cl.
*H01G 9/00* (2006.01)
*H01G 9/02* (2006.01)
(52) U.S. Cl. .................. 361/502; 252/62.2
(58) Field of Classification Search .......... 361/502; 252/62.2
See application file for complete search history.

(56) References Cited

U.S. PATENT DOCUMENTS

| | | | | |
|---|---|---|---|---|
| 5,414,117 A | * | 5/1995 | Armand et al. | 562/828 |
| 5,595,852 A | * | 1/1997 | Shimoda et al. | 430/108.24 |
| 5,627,292 A | * | 5/1997 | Armand et al. | 549/555 |
| 2007/0076349 A1 | | 4/2007 | Dementiev et al. | |
| 2008/0204974 A1 | * | 8/2008 | Yoshimitsu | 361/523 |

FOREIGN PATENT DOCUMENTS

EP 1380569 A1 * 1/2004

OTHER PUBLICATIONS

E. Frackowiak et al., Room-temperature Phosphonium Ionic Liquids for Supercapacitor Application, 164104-1-164104-3 (86 Applied Physics Letters)(2005).
A. Balducci, The Use of Ionic Liquids as Solvent-free Green Electrolytes for Hybrid Supercapacitors, 82 Applied Physics 627-632 (2006).
Z. Li et al., A New Room Temperature Ionic Liquid 1-butyl-3-trimethylsilylimidazolium Hexafluorophosphate as a Solvent for Extraction and Preconcentration of Mercury With Determination by Cold Vapor Atomic Spectrometry, 71 Talanta 68-72 (2007).

* cited by examiner

*Primary Examiner* — Eric Thomas
(74) *Attorney, Agent, or Firm* — Quarles & Brady LLP

(57) ABSTRACT

Disclosed are electrochemical double-layer capacitors having an electrode with a substrate and an electrolyte/quaternary ammonium salt capable of penetrating the substrate. Such salts have a moiety of the following formula:

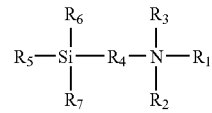

In one form all of the R groups are methyl. These electrodes appear particularly suitable for use at high voltages in applications such as electric and hybrid electric vehicles.

13 Claims, 3 Drawing Sheets

PRIOR ART

ORGANOSILICON AMINE-BASED ELECTROLYTES

CROSS-REFERENCE TO RELATED APPLICATIONS

This is a divisional application of U.S. Ser. No. 11/865,089 which was filed on Oct. 1, 2007, now abandoned.

STATEMENT REGARDING FEDERALLY SPONSORED RESEARCH/DEVELOPMENT

Not applicable.

BACKGROUND OF THE INVENTION

The present invention relates to ionic liquids useful as electrolytes in connection with energy storage devices such as supercapacitors. More particularly, it relates to organosilicon amine electrolytes.

Supercapacitors, sometimes also referred to in the literature as "electric double-layer capacitors", "electrochemical capacitors" or "ultracapacitors" are well known. Supercapacitors provide energy storage as well as pulse power delivery. This is useful in many applications, such as in connection with automotive starters and hybrid automotive vehicles.

One well known type of supercapacitor is depicted in FIG. 1. This drawing shows a supercapacitor 10 having two electrodes 11 which are kept from electrical contact with each other by a separator 12. There are current collectors 13 at opposite ends of the device. The electrodes consist of a porous material 14 and an electrolyte 15. Both the separator 12 and the porous material 14 are typically immersed in the electrolyte 15.

Current collecting plates 13 are in contact with the electrodes 11. Electrostatic energy is stored in polarized liquid layers, which form when a potential is applied across two of the electrodes. A "double layer" of positive and negative charges is formed at the electrode-electrolyte interface. The electrolyte allows ions to move freely through the separator.

To be optimally effective for certain applications, supercapacitors must, among other properties, have low internal resistance, store large amounts of charge, be physically strong, be stable at desired (preferably high) voltages, and be otherwise compatible with the usage environment. Therefore, there are many design parameters that must be considered in construction of such devices.

Aqueous and some organic electrolyte solutions have been proposed for use in supercapacitors. Aqueous electrolytes provide relatively low series resistance, improving the time constant of a supercapacitor and providing high power densities. However, they are often not stable at the operating voltages exceeding the electrolysis voltage of water (1.23 V).

Organic liquid electrolytes used in supercapacitors should preferably have higher ionic conductivity. As an example, acetonitrile provided high ionic conductivity. However, acetonitrile is a hazardous flammable and toxic material, which produces highly toxic products (HCN and CO) upon combustion and thermal decomposition.

Some other previously used organic liquid electrolytes have been based on alkyl carbonates (ethylene carbonate, propylene carbonate, and γ-butyrolactone, or dimethylcarbonate, diethylcarbonate, and ethylmethylcarbonate, for example) which are highly flammable. Some also have lower ionic conductivity as compared to aqueous electrolytes or electrolytes based on acetonitrile, and this causes higher internal losses of stored energy and power density of the supercapacitor.

In E. Frackowiak et al., Room-temperature Phosphonium Ionic Liquids For Supercapacitor Application, 164104-1-164104-3 (86 Applied Physics Letters)(2005) there was a discussion of using phosphonium salts for supercapacitor electrolytes, where the anion for such salts was $(CF_3SO_2)_2N^-$ ("TFSI").

In A. Balducci, The Use Of Ionic Liquids As Solvent-free Green Electrolytes For Hybrid Supercapacitors, 82 Applied Physics 627-632 (2006), there was a discussion of using that anion as part of salts containing cyclic cationic nitrogen moieties, as electrolytes for supercapacitors.

Our laboratory also recently reported, in U.S. patent application publication 2007/0076349, that polysiloxanes could have utility as electrolytes for supercapacitors and other energy storage devices.

In Z. Li et al., A New Room Temperature Ionic Liquid 1-butyl-3-trimethylsilylimidazolium Hexafluorophosphate As A Solvent For Extraction And Preconcentration Of Mercury With Determination By Cold Vapor Atomic Absorption Spectrometry, 71 Talanta 68-72 (2007) there was a discussion of using $PF_6^-$ as an anion with a cationic organosilicon compound having a cyclic nitrogen containing moiety, as a solvent for extraction.

Notwithstanding these developments in the art, there is a need for additional improvements with respect to electrolytes for supercapacitors.

SUMMARY OF THE INVENTION

In one aspect the invention provides an electrolyte comprising the following cationic moiety:

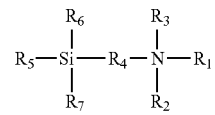

$R_1$, $R_2$ and $R_3$ are the same or different, and each is selected from the group consisting of alkyl moieties of less than ten carbons and hydrogen. At least one of $R_1$, $R_2$ and $R_3$ is an alkyl moiety. $R_4$ is selected from the group consisting of alkyl moieties of less than ten carbons (e.g. $CH_2$ or $C_3H_6$) and alkoxy groups of less than ten carbons.

$R_5$, $R_6$ and $R_7$ are the same or different and each is selected from the group consisting of alkyl moieties of less than ten carbons, hydrogen and —O—$SiR_8R_9R_{10}$. $R_8$, $R_9$ and $R_{10}$ are the same or different and each is selected from the group consisting of alkyl moieties with less than ten carbons and hydrogen.

There are four carbons directly linked to the nitrogen and they are only linked to each other through the nitrogen. This is important in connection with these compounds.

In a preferred form all of $R_1$, $R_2$ and $R_3$ are alkyl moieties with less than three carbons, $R_4$ is selected from the group consisting of alkyl moieties with less than three carbons, and $R_8$, $R_9$ and $R_{10}$ are all selected from the group consisting of alkyl moieties with less than three carbons. Even more preferably all of the R groups are alkyl moieties, all of them but $R_4$ are —$CH_3$ or —$C_2H_5$, and $R_4$ is $(CH_2)_n$ with n being less than 5.

These cations will be presented in supercapacitors as a portion of the electrolyte (together with an anion to create a salt). Preferred anions are halogen anions, $(CF_3SO_2)_2N^-$, $B(C_2O_4)_2^-$ and tetrafluoroborate anion, with $(CF_3SO_2)_2N^-$ being most preferred.

In another aspect the invention provides an electrochemical double-layer capacitor where the electrolyte is present as part of the supercapacitor's electrode system. This is expected to enable such a supercapacitor to operate at a voltage of 5.0 volts or above for extended periods.

The electrolytes of the present invention should have high room temperature ionic conductivity (hence providing low series resistance), high thermal and electrochemical stability (therefore high operating voltages and temperatures), and low volatility, toxicity and flammability. Particularly advantageous is that in some embodiments this permits operation at exceptionally high voltages.

In another aspect the invention provides a quaternary ammonium salt having the following formula:

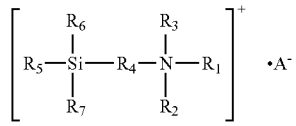

$R_1$, $R_2$ and $R_3$ are the same or different, and each is selected from the group consisting of alkyl moieties of less than ten carbons and hydrogen. At least one of $R_1$, $R_2$ and $R_3$ is an alkyl moiety. $R_4$ is selected from the group consisting of alkyl moieties of less than ten carbons (e.g. $CH_2$ or $C_3H_6$) and alkoxy groups of less than ten carbons.

$R_5$, $R_6$ and $R_7$ are the same or different and each is selected from the group consisting of alkyl moieties of less than ten carbons, hydrogen and —O—$SiR_8R_9R_{10}$. $R_8$, $R_9$ and $R_{10}$ are the same or different and each is selected from the group consisting of alkyl moieties with less than ten carbons and hydrogen. Also, A is an anion.

Our preferred electrolytes are relatively easy to make, and can be synthesized in high yields from available and relatively inexpensive starting materials. They are also stable in storage and processing.

The above and still other advantages of the present invention will be apparent from the description that follows. It should be appreciated that the following description is merely of the preferred embodiments of our invention. The claims should therefore be looked to in order to understand the full claimed scope of the invention.

DESCRIPTION OF THE PREFERRED EMBODIMENTS

Overview

The electrolytes of the present invention appear to have utility in a variety of energy storage devices. We prefer using them in supercapacitors, albeit there may be utility as well in other devices such as batteries and fuel cells.

We propose substituting our electrolytes for known liquid electrolytes in prior art conventional supercapacitors. Hence, the exact structure of the supercapacitors, apart from the electrolyte we propose to use therewith, does not appear critical.

Figure 1:
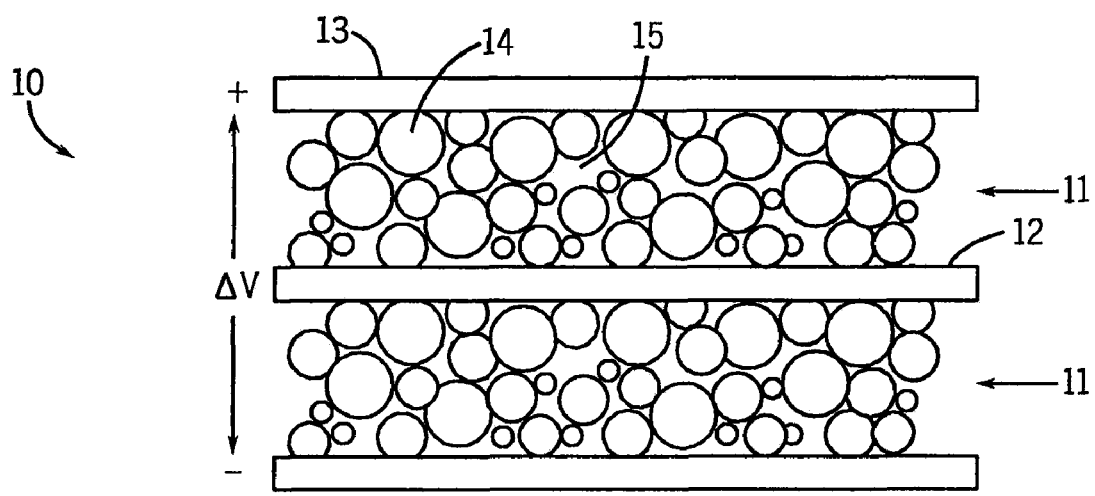
FIG. 1 depicts, in schematic form, a known structure for a supercapacitor.

As one example, we propose to use a FIG. 1 type supercapacitor. More details about this type of supercapacitor can be obtained from U.S. patent application publication 2007/0076349, the disclosure of which is incorporated by reference herein as if fully set forth herein.

Such supercapacitors have electrodes made in part of porous or other structured materials so that an electrolyte can easily penetrate the pores/structures, facilitating rapid ion motion and high conductivity. Electrons can then easily flow from the electrode to the current collector and vice versa. Nanostructured carbon electrodes are preferred.

Separators between electrodes for use in the supercapacitors of the present invention can be of conventional structure. For example, they can be made of polymer film of porous structure such as PE, PP, or PTFE films, or other known materials which have been used as a separator in a supercapacitor.

On the exterior surface of the electrode/separator "sandwich" we prefer to position current collectors which are electro-conductive metal plates or films, like aluminum, nickel, copper, molybdenum, titanium, steel, or any other known electro-conductive material which can be used as a current collector in supercapacitors.

Synthesis Of Electrolytes

We next describe below synthesis and testing of our preferred electrolytes.

EXAMPLE 1

In this example, we first synthesize an intermediate $[Me_3Si—(CH_2)—N(CH_2CH_3)_2]$ ("TMSC1NEt$_2$"). Iodomethyltrimethylsilane (32 g, 0.14 mol) was refluxed at room temperature with excess diethyl amine ($CH_3NEt_2$) (44 g, 4 equiv.) for 16 h. After recovering the excess starting amine by distillation, the residue was dissolved in $CHCl_3$ and washed with saturated potassium carbonate solution. The organic phase was then dried over $MgSO_4$, followed by removing the solvent by rotary evaporation.

The pure intermediate ("TMSC1NEt$_2$") was obtained by factional distillation as colorless liquid. 16 g, 69% yield. b.p. 140-141° C. $^1$H NMR (300 MHz, CDCl): δ=0.029 (s, 9H, $Si(CH_3)_3$), 0.975 (t, J=7.2 Hz, 6H, $CH_3CH_2N$), 1.924 (s, 2H, $TMSCH_2$), 2.475 (q, J=7.2 Hz, 4H, $NCH_2CH_3$); $^{13}$C NMR (300 MHz, CDCl3): 0, 12.93, 45.99, 51.57; $^{29}$Si NMR (500 MHz, CDCl3): −2.423.

EXAMPLE 2

In this example we synthesized a second intermediate $[Me_3Si—(CH_2)_3—N(CH_2CH_3)_2]$ ("TMSC3NEt$_2$") using a similar approach, but with the starting silane instead being $Me_3Si—(CH_2)_3—I$. $^1$H NMR (300 MHz, CDCl): δ=−0.03 (s, 9H, $Si(CH_3)_3$), 0.42 (m, 2H, $TMSCH_2$), 1.005 (t, J=7.2 Hz, 6H, $CH_3CH_2N$), 1.972-1.481 (m, 2H, $TMSCH_2CH_2$), 2.37 (t, J=8.0 Hz, 2H, $TMSCH_2CH_2CH_2$), 2.50 (q, J=7.2 Hz, 4H, $NCH_2CH_3$); $^{13}$C NMR (300 MHz, CDCl3): 0, 13.44, 16.09, 23.38, 48.66, 58.55; $^{29}$Si NMR (500 MHz, CDCl3): 0.003.

EXAMPLE 3

Figure 2:
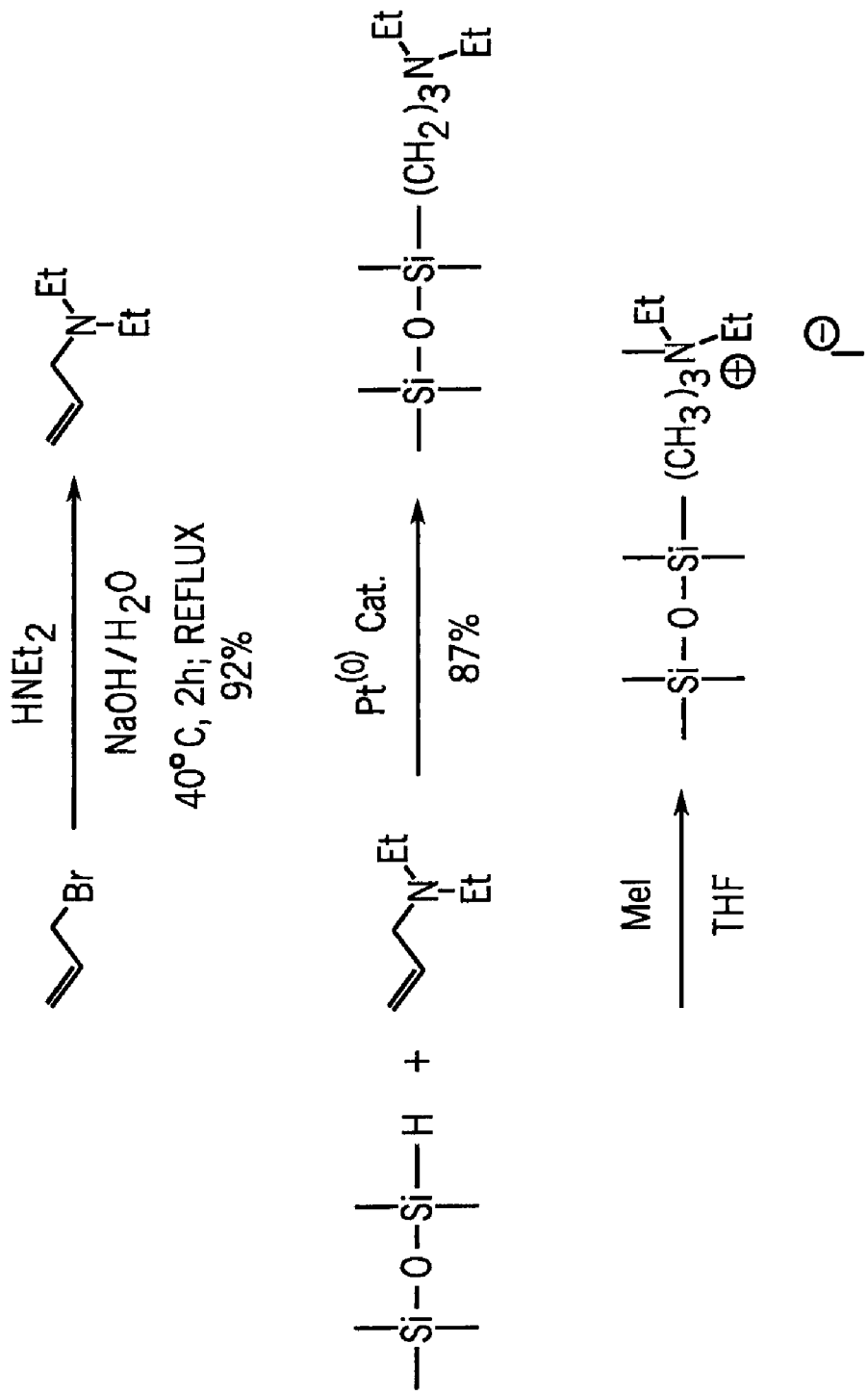
FIG. 2 depicts a synthesis, in schematic form, of one of the electrolytes of the present invention.

In this example we synthesized a third intermediate $[Me_3Si—O—Si\quad (CH_3)_2(CH_2)_3—N(CH_2CH_3)_2]$ ("2SC3NEt$_2$"). As shown in FIG. 2, to create N,N-diethyl allylamine we added diethylamine (73.2 g, 1 mol) to NaOH solution (44 g, 1.1 mol) in 400 mL water. The mixture was heated to 40° C. To the mixture allyl bromide was added slowly (128 g, 1.05 mol) over 1.5 h.

The reaction was heated to reflux for 16 h. After being cooled down to room temperature, the product was extracted with ether and neutralized with saturated potassium carbonate solution. After drying over with magnesium sulfate, all volatiles were removed by rotary evaporation. The pure N,N-diethyl allylamine intermediate product was distilled to yield 105 g (92%) of pure product.

To a mixture of pentamethyldisiloxane (86 g, 0.42 mol) and Karstedt's catalyst (100 μl), was added the N,N-diethyl allylamine (48 g, 0.4 mol) at 0° C. under a nitrogen atmosphere. The reaction was then heated to 80° C. for 16 h.

The colorless intermediate was obtained by vacuum distillation. $^1$H NMR (300 MHz, CDCl): δ=0.026 (s, 6H, Si(CH$_3$)$_3$), 0.037 (s, 9H, TMS-O—Si(CH$_3$)$_2$), 0.409-0.465 (m, 2H, TMSOSi—CH$_2$), 1.01 (t, J=7.2 Hz, 6H, CH$_3$CH$_2$N), 1.4-1.4-1.5 (m, 2H, CH$_2$CH$_2$Si), 2.39 (t, J=8.0 Hz, 2H, CH$_2$CH$_2$Si), 2.52 (q, J=7.2 Hz, 4H, NCH$_2$CH$_3$); $^{13}$C NMR (300 MHz, CDCl3): 0, 1.645, 11.44, 15.79, 20.58, 46.68, 56.30; $^{29}$Si NMR (500 MHz, CDCl3): 5.981, 6.388.

EXAMPLE 4

In this example we synthesized, in a similar manner, a fourth intermediate [Me$_3$Si—O—Si(CH$_3$)$_2$—(CH$_2$)—N(CH$_2$CH$_3$)$_2$] ("2SC1NEt$_2$") using techniques analogous to those used for Example 3, but with a different amine starting material. $^1$H NMR (300 MHz, CDCl): δ=0.050 (s, 9H, Si(CH$_3$)$_3$), 0.093 (s, 6H, TMS-O—Si(CH$_3$)$_2$), 0.96 (t, J=7.2 Hz, 6H, CH$_3$CH$_2$N), 1.873 (s, 2H, CH$_2$SiO), 2.46 (q, J=7.2 Hz, 4H, NCH$_2$CH$_3$); $^{13}$C NMR (300 MHz, CDCl3): 0, 12.93, 45.99, 51.57; $^{29}$Si NMR (500 MHz, CDCl3): -2.423.

Example 5

As a first example of our cations of the present invention, we prepared an iodine salt where the cation was [Me$_3$Si—(CH$_2$)—N(CH$_3$)(CH$_2$CH$_3$)$_2$]$^+$ ("TMSC1ILI"). To a solution of the Example 1 intermediate (53 g, 0.33 mol) in 200 mL THF was added slowly methyl iodide (65 g, 0.46 mol) at 0° C. After addition, the reaction was refluxed for 16 h.

The products were precipitated from dry ether, and purified by recrystallization from CHCl$_3$/Et$_2$O to yield 82 g, 82% of pure salt. $^1$H NMR (300 MHz, CDCl): δ=0.32 (s, 9H, Si(CH$_3$)$_3$), 1.41 (t, J=7.2 Hz, 6H, CH$_3$CH$_2$N), 3.20 (s, 2H, TMSCH$_2$), 3.29 (s, 3H, NCH$_3$), 3.60 (q, J=7.2 Hz, 4H, NCH$_2$CH$_3$); $^{13}$C NMR (300 MHz, CDCl3): 0, 9.25, 51.70, 55.76, 60.36; $^{29}$Si NMR (500 MHz, CDCl3): -1.94.

EXAMPLE 6

As a second example of our cations, we prepared an iodine salt where the cation was [Me$_3$Si—(CH$_2$)$_3$—N (CH$_3$)(CH$_2$CH$_3$)$_2$]$^+$ ("TMSC3ILI"), using a similar procedure, but with the Example 2 product as a starting material. $^1$H NMR (300 MHz, CDCl): δ=0.03 (s, 9H, Si(CH$_3$)$_3$), 0.50-0.56 (m, 2H, TMSCH$_2$), 1.38 (t, J=7.4 Hz, 6H, CH$_3$CH$_2$N), 1.60-1.70 (m, 2H, TMSCH$_2$CH$_2$), 3.26 (s, 3H, NCH$_3$), 3.36-3.42 (m, 2H, TMSCH$_2$CH$_2$CH$_2$), 3.60 (q, J=7.2 Hz, 4H, NCH$_2$CH$_3$); $^{13}$C NMR (300 MHz, CDCl3): 0001, 10.22, 14.79, 18.99, 49.89, 58.54, 65.38; $_{29}$Si NMR (500 MHz, CDCl3): 0.98.

EXAMPLE 7

As a third example of our cations, we prepared an iodine salt where the cation was [Me$_3$Si—(CH$_2$)$_3$—N(CH$_2$CH$_3$)$_3$]$^+$ ("TMSC3NEt3ILI"), using Et$_3$N directly to react with Me$_3$Si—(CH$_2$)$_3$—I. $^1$H NMR (300 MHz, CDCl): δ=0.02 (s, 9H, Si(CH$_3$)$_3$), 0.49-0.55 (m, 2H, TMSCH$_2$), 1.37 (t, J=7.4 Hz, 9H, CH$_3$CH$_2$N), 1.58-1.68 (m, 2H, TMSCH$_2$CH$_2$), 3.22-3.27 (m, 2H, TMSCH$_2$CH$_2$CH$_2$), NCH$_3$), 3.48 (q, J=7.2 Hz, 6H, NCH$_2$CH$_3$); $^{13}$C NMR (300 MHz, CDCl3): 0001, 10.01, 14.94, 18.76, 55.43, 55.46, 55.49, 62.12; $^{29}$Si NMR (500 MHz, CDCl3).

EXAMPLE 8

As a fourth example of our cations, we prepared an iodine salt where the cation was [Me$_3$Si—O—Si(CH$_3$)$_2$—(CH$_2$)—N(CH$_3$)(CH$_2$CH$_3$)$_2$]$^+$ ("2SC1ILTI"), using a similar procedure, but starting with the compound of Example 4.

EXAMPLE 9

As a fifth example of our cations, we prepared an iodine salt where the cation was [Me$_3$Si—O—Si(CH$_3$)$_2$—(CH$_2$)$_3$—N(CH$_3$)(CH$_2$CH$_3$)$_2$]$^+$ ("2SC3ILTI"), using a similar procedure, but starting with the compound of Example 3.

EXAMPLE 10

We then, through anion exchange techniques, synthesized preferred salts using the same cations. As a first example, we took the Example 5 salt and replaced the iodine with the TFSI anion ("TMSC1ILTFSI"). The salt of Example 5 (30 g, 0.1 mol) and LiTFSI (24 g, 0.12 mol) were dissolved in 60 mL dry acetone, and stirred at room temperature for 4 h. After removing the solvent by rotary evaporation, the residue was dissolved in chloroform/water mixture. The organic phase was separated, washed subsequently with water, dilute sodium thiosulfate solution, dilute AgNO$_3$ solution and water, and then dried over MgSO$_4$.

TMSC1ILTFSI (the salt of Example 5, but with a TFSI anion replacing the iodine anion) was obtained after evaporating the solvent, and thoroughly dried in vacuo at 100° C. for 48 h. $^1$H NMR (300 MHz, CDCl): δ=0.29 (s, 9H, Si(CH$_3$)$_3$), 1.38 (t, J=7.2 Hz, 6H, CH$_3$CH$_2$N), 2.92 (s, 2H, TMSCH$_2$), 3.04 (s, 3H, NCH$_3$), 3.36 (q, J=7.2 Hz, 4H, NCH$_2$CH$_3$); $^{13}$C NMR (300 MHz, CDCl3): 0, 9.04, 51.54, 56.38, 60.87, 120.7 (q, JC-F=Hz); $^{29}$Si NMR (500 MHz, CDCl3): -1.58

EXAMPLE 11

("TMSC3ILTFSI") was synthesized by treating the salt of Example 6 in a manner similar to how the salt of Example 5 was treated, so as to yield the Example 6 salt albeit with the iodine anion replaced with a TFSI anion. Colorless liquid, yield: 80%. $^1$H NMR (300 MHz, CDCl): δ=0.03 (s, 9H, Si(CH$_3$)$_3$), 0.42-0.546 (m, 2H, TMSCH$_2$), 1.37 (t, J=7.4 Hz, 9H, CH$_3$CH$_2$N), 1.58-1.68 (m, 2H, TMSCH$_2$CH$_2$), 2.98 (s, 3H, NCH$_3$), 3.22-3.27 (m, 2H, TMSCH$_2$CH$_2$CH$_2$), NCH$_3$), 3.48 (q, J=7.2 Hz, 6H, NCH$_2$CH$_3$); $^{13}$C NMR (300 MHz, CDCl3): 0.0, 9.71, 14.92, 19.0, 49.23, 58.64, 65.88, 122 (q, JC-F=Hz); $^{29}$Si NMR (500 MHz, CDCl3): 0.98.

EXAMPLE 12

("2SC1ILTFSI") was synthesized by treating the salt of Example 8 in a similar manner to yield a salt of the same formula but for the iodine anion being replaced with a TFSI anion. Colorless liquid, yield: 85%. $^{13}$H NMR (300 MHz, CDCl): δ=0.12 (s, 9H, Si(CH$_3$)$_3$), 0.31 (s, 6H, Si(CH$_3$)$_2$OSi), 1.35 (t, J=7.4 Hz, CH$_3$CH$_2$N), 2.82 (s, NCH$_3$SiO), 3.05, (s, 3H, NCH$_3$), 3.40 (q, 4H, J=7.2 Hz, NCH$_2$CH$_3$); $^{13}$C NMR (300 MHz, CDCl3) 0.28, 0.30, 6.87, 53.27, 58.70, 118.6 (q, JC-F=Hz); $^{29}$Si NMR (500 MHz, CDCl3): −0.03, 12.44.

EXAMPLE 13

("2SC3ILTFSI") was synthesized by treating the salt of Example 9 in a similar manner to yield a salt of the same formula but for the iodine anion being replaced with a TFSI anion. Colorless liquid, yield: 86%. $^1$H NMR (300 MHz, CDCl): δ=0.03 (s, 9H, Si(CH$_3$)$_3$), 0.06 (s, 6H, Si(CH$_3$)$_2$OSi), 1.33 (t, J=7.2 Hz, CH$_3$CH$_2$N), 1.57-1.69 (m, 2H, CH$_2$CH$_2$Si), 3.05 (s, 3H, NCH$_3$), 3.20 (m, 2H, CH$_2$CH$_2$CH$_2$Si), 3.41 (q, 4H, J=7.2 Hz, NCH$_2$CH$_3$); $^{13}$C NMR (300 MHz, CDCl3) 0.02, 1.74, 7.82, 14.20, 16.27, 47.42, 56.53, 63.09, 119.6 (q, JC-F=Hz); $^{29}$Si NMR (500 MHz, CDCl3): −0.03, 12.44.

EXAMPLE 14

("TMSC1ILBOB") was synthesized by treating the salt of Example 5 in a manner similar to Example 10, but using LiBOB instead of LiTFSI. This replaced the iodine anion with the BOB anion. $^1$H NMR (300 MHz, CDCl): δ=0.31 (s, 9H, Si(CH$_3$)$_3$), 1.42 (t, J=7.2 Hz, 6H, CH$_3$CH$_2$N), 2.98 (s, 2H, TMSCH$_2$), 3.10 (s, 3H, NCH$_3$), 3.42 (q, J=7.2 Hz, 4H, NCH$_2$CH$_3$); $^{13}$C NMR (300 MHz, CDCl3): 0, 9.06, 51.53, 51.58, 51.63, 56.36, 60.89, 159.45; 11B NMR: 5.23; $^{29}$Si NMR (500 MHz, CDCl3): −1.94.

EXAMPLE 15

("TMSC3ILBOB") was synthesized by treating the salt of Example 6 in a manner similar to Example 11, but using LiBOB instead of LiTFSI. This replaced the iodine anion with the BOB anion. Colorless liquid, yield: 82%. $^1$H NMR (300 MHz, CDCl): δ=0.02 (S, 9H, Si(CH$_3$)$_3$), 0.46-0.52 (m, 2H, TMSCH$_2$), 1.38 (t, J=7.4 Hz, 6H, CH$_3$CH$_2$N), 1.61-1.72 (m, 2H, TMSCH$_2$CH$_2$) 3.03 (s, 3H, NCH$_3$), 3.17-3.22 (m, 2H, TMSCH$_2$CH$_2$CH$_2$), NCH$_3$), 3.38 (q, J=7.2 Hz, 6H, NCH$_2$CH$_3$); $^{13}$C NMR (300 MHz, CDCl3): 0.0, 9.83, 14.97, 19.0, 49.42, 58.68, 65.79, 160.75 (q, JC-F=Hz); $^{29}$Si NMR (500 MHz, CDCl3): 1.04.

EXAMPLE 16

("2SC1ILBOB") was synthesized by treating the salt of Example 8 in a manner similar to Example 12, but using LiBOB instead of LiTFSI. This replaced the iodine anion with the BOB anion. Colorless liquid, yield: 87%. $^1$H NMR (300 MHz, CDCl): δ=0.14 (s, 9H, Si(CH$_3$)$_3$), 0.33 (s, 6H, Si(CH$_3$)$_2$OSi), 1.40 (t, J=7.4 Hz, CH$_3$CH$_2$N), 2.86 (s, NCH$_2$SiO), 3.11, (S, 3H, NCH$_3$), 3.44 (q, 4H, J=7.2 Hz, NCH$_2$CH$_3$); $^{13}$C NMR (300 MHz, CDCl3) 0.0, 0.21, 6.85, 49.21, 53.20, 58.62, 53157.27; $^{29}$Si NMR (500 MHz, CDCl3): −0.19, 12.79.

EXAMPLE 17

A carbon analog (C6ILTFSI) of a silicon-containing ionic liquid, (diethyl hexyl methyl ammonium bis(trifluoromethane sulfonyl) imide), was then synthesized for use in the testing described below. Diethyl hexyl methyl ammonium iodide (C6ILI) was first synthesized by reacting hexyl iodide with methyl diethyl amine. The crude C6ILI was then purified one time by recrystallization from tetrahydrofuran. C6ILTFSI was then synthesized in a manner similar to Example 5, so as to yield the salt with a TFSI anion. Colorless liquid, yield: 78%. $^1$H NMR (300 MHz, CDCl): δ=0.87 (t, 3H, J=7.2 Hz, CH$_3$(CH$_2$)$_5$), 1.29-1.34 (m, 12H, (CH$_2$)$_3$CH$_3$ and CH$_3$CH$_2$N), 1.56-1.66 (m, 2H, CH$_2$(CH$_2$)$_3$CH$_3$), 2.93 (s, 3H, NCH$_3$), 3.10-3.15 (m, 2H, CH$_2$(CH$_2$)$_4$CH$_3$), 3.30 (q, 4H, J=7.2 Hz, NCH$_2$CH$_3$); 13C NMR (300 MHz, CDC$^{13}$): 7.72, 13.81, 22.10, 25.88, 31.11, 47.36, 56.78, 61.07, 120 (q, J$_{C-F}$=321.2 Hz).

Test Results

In the following table are listed dielectric constants, viscosities, and glass transition temperatures of various of our preferred ionic liquids. The glass transition temperatures were determined by differential scanning calorimetry. Tm is the melting point: only the first compound exhibited a melting point. All of the other compounds had only glass transition temperatures.

TABLE 1

|  | ε | η(cP) | T$_g$ (° C.) | T$_m$ (° C.) |
|---|---|---|---|---|
| TMSC1ILTFSI | — | — | −26 | 50 |
| TMSC1ILBOB | — | — | −37 | na |
| TMSC3ILTFSI | 1.06 | 257 | −64 | na |
| TMSC3ILBOB | 1.17 | 454 | −29 | na |
| 2SC1ILTFSI | 1.00 | 197 | −77 | na |
| 2SC1ILBOB | 1.08 | 414 | −60 | na |
| 2SC3ILTFSI | 1.18 | 273 | −74 | na |
| 2SC3ILBOB | 1.93 | 1236 | −47 | na |

Electrical Characterization: Linear sweep voltammetry was then performed using a potentialstat (Solartron 1260) and impedance analyzer (Solartron 1287) in an argon-filled glove box, with a 10 mL beaker-type three-electrode cell equipped with a glassy carbon electrode (surface area: 7.85×10$^{-3}$ cm$^{-2}$), a Ag wire counter electrode, and Ag/Ag$^+$ reference electrode consisting of Ag wire, 50 μL 1M AgNO$_3$ acetonitrile solution and 450 μL C6ILTFSI ionic liquid. The potential was referred to ferrocene (Fc)/ferrocenium (Fc$^+$) redox couple in each salt. The data for each salt was collected in the first cathodic and anodic scan at 25° C.

Figure 3:
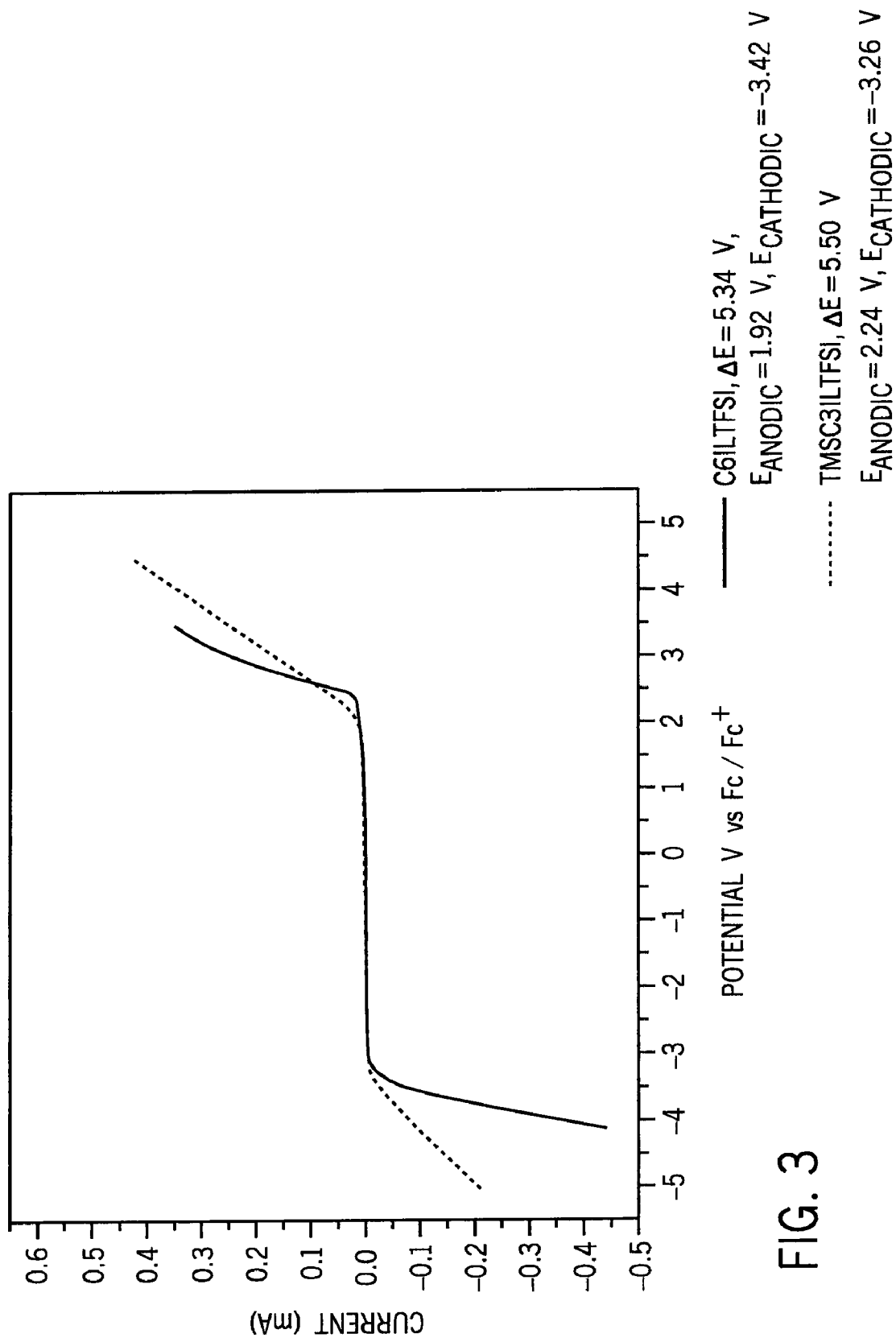
FIG. 3 depicts test results.

FIG. 3 depicts a linear sweep voltammogram of ionic liquids on a glassy carbon electrode (surface area: 7.85×10$^{-3}$ cm$^{-2}$) at 25° C.; scan rate: 50 mV/s; counter electrode: silver wire; potential (V) was referenced to ferrocene (Fc)/ferrocenium (Fc$^+$) redox couple.

The silicon-containing ionic liquid TMSC3ILTFSI exhibited a desirable electrochemical window, one which was even higher than the carbon analog, C6ILTFSI. At both ends of oxidative and reductive process, TMSC3ILTFSI decomposes more slowly than C6ILTFSI.

Other Embodiments

While various embodiments of the present invention have been described above, the present invention is not limited to just these disclosed examples. There are other modifications that are meant to be within the scope of the invention and claims. For example, it is expected that a variety of other organosilicon amine-based compounds with less than thirty total carbons will also have desirable electrolyte characteristics.

Thus, the claims should be looked to in order to judge the full scope of the invention.

INDUSTRIAL APPLICABILITY

The present invention provides improved electrolytes, and improved supercapacitors which use these electrolytes.

We claim:

1. An electrochemical double-layer capacitor having an electrode comprising:
    a substrate; and
    an electrolyte penetrating the substrate comprising a cationic moiety comprising the following structure:

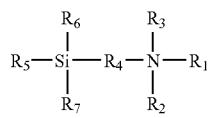

wherein $R_1$, $R_2$ and $R_3$ are the same or different and each is selected from the group consisting of alkyl moieties of less than ten carbons and hydrogen, wherein at least one of $R_1$, $R_2$ and $R_3$ are alkyl moieties;
    wherein $R_4$ is selected from the group consisting of alkyl moieties of less than ten carbons; and
    wherein $R_5$, $R_6$ and $R_7$ are the same or different and each is selected from the group consisting of alkyl moieties of less than ten carbons and hydrogen.

2. The electrochemical double-layer capacitor of claim 1, wherein all of $R_1$, $R_2$ and $R_3$ are alkyl moieties with less than three carbons.

3. The electrochemical double-layer capacitor of claim 1, wherein $R_4$ is selected from the group consisting of alkyl moieties with less than three carbons.

4. The electrochemical double-layer capacitor of claim 1, wherein all of $R_1$, $R_2$, $R_3$, $R_4$, $R_5$, $R_6$ and are alkyl moieties.

5. The electrochemical double-layer capacitor of claim 4, wherein all of $R_1$, $R_2$, $R_3$, $R_5$, $R_6$ and are —$CH_3$ or —$C_2H_5$.

6. The electrochemical double-layer capacitor of claim 1, wherein $R_4$ is $(CH_2)_n$ and n is less than 5.

7. The electrochemical double-layer capacitor of claim 1, further comprising an anion such that the cation is present in a salt.

8. The electrochemical double-layer capacitor of claim 7, wherein the anion is selected from the group consisting of halogen anions, $(CF_3SO_2)_2N^-$, $B(C_2O_4)_2^-$ and tetrafluoroborate anion.

9. The electrochemical double-layer capacitor of claim 8, wherein the anion is $(CF_3SO_2)_2N^-$.

10. The electrochemical double-layer capacitor of claim 1, wherein the capacitor is capable of operating at a voltage of 5.0 volts or above.

11. An electrochemical double-layer capacitor having an electrode comprising:
    a substrate; and
    a quaternary ammonium salt penetrating the substrate and having the following formula:

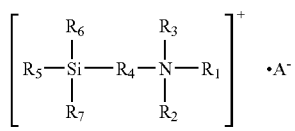

wherein $R_1$, $R_2$ and $R_3$ are the same or different and each is selected from the group consisting of alkyl moieties of less than ten carbons and hydrogen, wherein at least one of $R_1$, $R_2$ and $R_3$ are alkyl moieties;
    wherein $R_4$ is selected from the group consisting of alkyl moieties of less than ten carbons;
    wherein $R_5$, $R_6$ and $R_7$ are the same or different and each is selected from the group consisting of alkyl moieties of less than ten carbons and hydrogen; and
    wherein A is an anion.

12. The electrochemical double-layer capacitor of claim 11, wherein the anion is selected from the group consisting of halogen anions, $(CF_3SO_2)_2N^-$, $B(C_2O_4)_2^-$ and tetrafluoroborate anion.

13. An electrode suitable for use in an electrochemical double-layer capacitor, the electrode comprising:
    a substrate; and
    an electrolyte penetrating the substrate comprising a cationic moiety comprising the following structure:

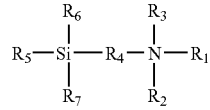

wherein $R_1$, $R_2$ and $R_3$ are the same or different and each is selected from the group consisting of alkyl moieties of less than ten carbons and hydrogen, wherein at least one of $R_1$, $R_2$ and $R_3$ are alkyl moieties;
    wherein $R_4$ is selected from the group consisting of alkyl moieties of less than ten carbons; and
    wherein $R_5$, $R_6$ and $R_7$ are the same or different and each is selected from the group consisting of alkyl moieties of less than ten carbons and hydrogen.

* * * * *